United States Patent [19]

Szonntagh

[11] 4,280,889
[45] Jul. 28, 1981

[54] SOLID STATE ION RESPONSIVE AND REFERENCE ELECTRODES

[75] Inventor: Eugene L. Szonntagh, Flourtown, Pa.

[73] Assignee: Honeywell Inc., Minneapolis, Minn.

[21] Appl. No.: 874,660

[22] Filed: Feb. 2, 1978

Related U.S. Application Data

[63] Continuation-in-part of Ser. No. 666,166, Mar. 11, 1976, abandoned, which is a continuation-in-part of Ser. No. 552,284, Feb. 24, 1975, abandoned.

[51] Int. Cl.³ .......................................... G01N 27/30
[52] U.S. Cl. ............................ 204/195 F; 204/195 R; 204/195 G; 204/195 M; 204/195 S; 204/195 B
[58] Field of Search .......... 204/195 R, 195 G, 195 M, 204/195 S, 195 F, 195 B, 1 S, 1 H, 1 A, 192 R, 192 C, 192 SP; 128/2 E; 324/29, 30 R

[56] References Cited

U.S. PATENT DOCUMENTS

| | | | |
|---|---|---|---|
| 3,133,872 | 5/1964 | Miller et al. | 204/196 |
| 3,443,311 | 5/1969 | Worobey | 204/192 SP |
| 3,498,901 | 3/1970 | Metz et al. | 204/195 G |
| 3,718,569 | 2/1973 | Peterson et al. | 204/195 G |
| 3,856,649 | 12/1974 | Genshaw et al. | 204/195 F |
| 4,053,381 | 10/1971 | Hamblen et al. | 204/195 M |

OTHER PUBLICATIONS

P. D. Davidse et al., Insulation, pp. 41-43, Apr. 1966.

Primary Examiner—G. L. Kaplan
Attorney, Agent, or Firm—Laurence J. Marhoefer; Lockwood D. Burton; Mitchell J. Halista

[57] ABSTRACT

A solid state ion concentration measuring electrode having the ion concentration measuring electrode structure formed by successive layers on an insulating substrate with an outer ion sensitive glass layer being deposited on a substantially thermally matched supporting solid electrolyte layer by RF sputtering. The reference electrode is similarly formed by depositing an outer layer of glass onto a supporting solid electrolyte layer by RF sputtering with the temperature expansion of the glass and supporting solid electrolyte structure being selected to produce a differential expansion causing random cracking of the glass layer during temperature cycling of the referenece electrode. A combination structure is provided wherein the ion concentration measuring electrode and the reference electrode are formed on opposite sides of the same electrically insulating substrate with a thermal compensating element being included in the integrated package.

41 Claims, 3 Drawing Figures

SOLID STATE ION RESPONSIVE AND REFERENCE ELECTRODES

CROSS-REFERENCE TO CO-PENDING APPLICATION

The present application is a continuation-in-part of Ser. No. 666,166 filed on Mar. 11, 1976 which was a continuation application of Ser. No. 552,284, filed on Feb. 24, 1975 and both now abandoned.

BACKGROUND OF THE INVENTION

1. Field of the Invention

The present invention relates to ion concentration measuring apparatus. More specifically, the present invention is directed to a solid state ion responsive electrode and reference electrode.

2. Description of the Prior Art

Conventional ion concentration measuring electrode structures have usually used a glass measuring electrode, a reference electrode and a thermal compensator. For example, various types of special glasses have been used to measure the pH of aqueous solutions. In making these glass electrodes the pH sensitive glass is usually fused to the end of a less expensive glass tube and is subsequently blown into a small bulb of about two to four mils thick. These "hand-blown" pH glass electrodes are fragile, have very high electrical impedance due to the thickness of the glass and are used for limited temperature ranges mainly because of the internal pressure developed by a liquid electrolyte fill which is subsequently introduced into the interior of the pH measuring electrode to provide an electrically conductive ion source. An example of a typical prior art pH electrode apparatus is shown in U.S. Pat. No. 3,405,048 of D. J. Soltz. These prior art glass electrodes are expensive mainly because of the extensive use of highly skilled manual labor in the construction of the glass envelope and the subsequent filling thereof. A somewhat similar construction is used in the construction of the prior art reference cell which additionally increases the cost of the overall conventional pH measuring system. Despite its disadvantages, the glass electrode has retained its popularity in the field of ion concentration measurement even after attempts to develop a solid state electrode such as that shown in U.S. Pat. No. 3,498,901 of L. T. Metz et al since the response of the glass electrode is faster than other prior art devices with the glass electrode also having the broadest useful pH range. However, in order to provide a low cost and even more useful ion concentration measuring system it is desirable to produce a low impedance, high reliability and relatively unbreakable ion concentration measuring electrode.

SUMMARY OF THE INVENTION

An object of the present invention is to provide an improved solid state ion responsive electrode structure and reference electrode structure.

Another object of the present invention is to provide an improved combination ion concentration measuring electrode and reference electrode structure.

In accomplishing this and other objects, there has been provided, in accordance with the present invention, a solid state ion concentration and reference electrode structure having an ion measuring electrode with an insulating substrate supporting an electrically conductive structure overlaid with a solid electrolyte layer and having a final ion responsive layer attached to the solid electrolyte layer by RF sputtering. In the reference electrode, an outer glass layer is supported on a solid electrolyte layer and has a coefficient of thermal expansion different from the supporting solid electrolyte layer while in the ion measuring electrode, the outer ion responsive layer is substantially thermally matched to the supporting electrolyte layer.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Figure 1:
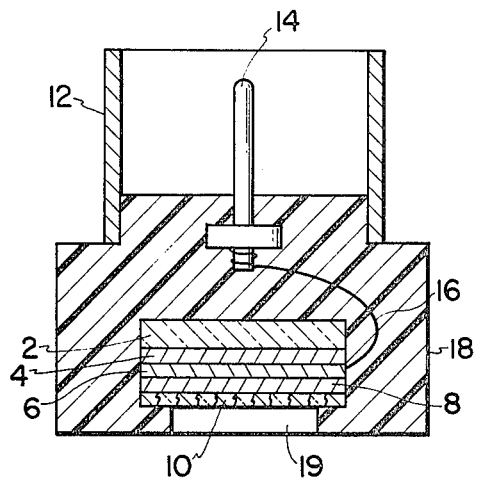
FIG. 1 is a pictorial illustration of a cross-section of an example of a reference electrode embodying the present invention.

Referring to FIG. 1 in more detail, there is shown a pictorial illustration of a cross-section of an example of a reference electrode embodying the present invention. An electrically insulation substrate 2 of an electrically insulating material, e.g., ceramic or glass, has a first layer 4 of chromium (Cr) deposited on one side thereof. A second layer 6 of silver (Ag) is subsequently deposited on the chromium and a third layer 8 of silver chloride (AgCl) is deposited on the silver. An outer layer 10 of a suitable glass is RF sputtered on the exposed surface of the silver chloride layer 8. The glass material for the outer layer 10 is selected to have a coefficient of thermal expansion different from the supporting silver chloride structure 8 whereby a subsequent temperature cycling of the multilayer structure is effective to produce microscopic cracks in the outer glass layer. For example, borosilicate glass has a coefficient approximately 1/10 that of silver chloride. These cracks provide ion conduction paths to the silver chloride layer from an aqueous solution in which the reference electrode is immersed during ion concentration measurements. A socket shell 12 is arranged to enclose a single contact pin 14. The contact pin is electrically connected by an electrically conducting wire 16 to the silver layer 6 of the multilayer structure. An encapsulating, or potting, compound 18 is subsequently applied to the multilayer structure, the socket shell 12, the contact pin 14 and the connecting wire 16 to form a moisture-proof barrier and to unite the elements into a rigid package. An open window, or hole, 19 is formed through the potting compound 18 to expose the outer glass layer 10.

Figure 2:
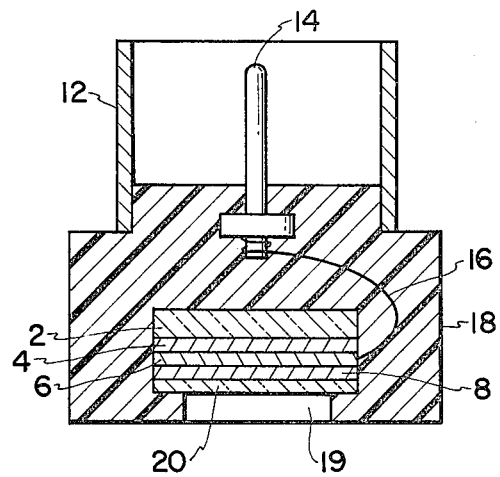
FIG. 2 is a pictorial illustration of a cross-section of an example of an ion concentration measuring electrode embodying the present invention.

In FIG. 2, there is shown a pictorial illustration of a cross-section of an exemplary pH measuring electrode embodying the present invention. Similar reference numbers have been used in FIGS. 1 and 2 to indicate similar structural elements although the combination of FIG. 2 is directed toward a different device from that shown in FIG. 1. An electrically insulating substrate 2, e.g., glass or ceramic, is used as a support member for a multi-layer structure similar to that used in the reference electrode. Specifically, the glass substrate 2 is first plated with a first layer 4 of chromium which is followed by a second layer 6 of silver and a subsequent third layer 8 of silver chloride. An outer layer 20 of pH sensitive glass is then RF sputtered by conventional means on the silver chloride layer. The temperature coefficient of the silver chloride and pH glass layer are matched whereby the pH glass will not produce microscopic cracks as during normal temperature cycling, e.g., 0° to 100° C., as in the case of outer glass layer used in the reference electrode previously described. For example, Corning 1990 glass has a coefficient of thermal expansion approximately one-half that of silver chloride. Other pH sensitive glasses can be produced to even more closely match the coefficient of thermal expansion of the silver chloride layer by using glass formulas with the following characteristics: a high coefficient of expansion can be achieved by using oxides such as $Li_2O$, $Na_2O$, $K_2O$, $Rb_2O$, $Cs_2O$, BaO and SrO while a low coefficient of expansion can be achieved by using $SiO_2$, $B_2O_3$, $Al_2O_3$, BeO and $TiO_2$. Thus, the coefficient of thermal expansion of the silver chloride layer or other solid state electrolyte materials such as CuO, AgI, RbI, $RbAg_4I_5$, etc. can be matched to an even closer approximation if either the temperature cycling during the measurement operation or the electrolyte material layer imposes a need for such a match. The thickness of the pH glass is approximately 10 to 10K Å. A thermal compensator structure may be produced using an insulating substrate with a thermal sensitive element mounted therein and having the same overall configuration as that used for the aforesaid reference and pH electrodes whereby the three elements would be used concurrently as shown in the aforesaid Soltz U.S. Pat. No. 3,405,048.

Figure 3:
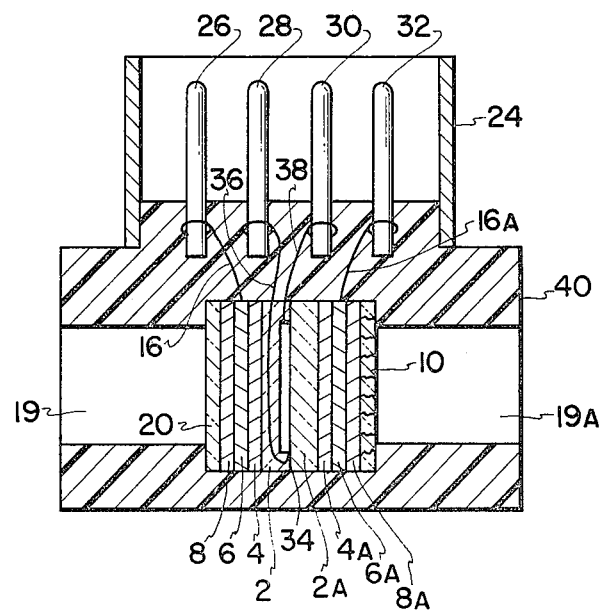
FIG. 3 is a pictorial illustration of a cross-section of an example of a combination ion responsive, reference electrode and thermal compensator embodying the present invention.

In order to further utilize the solid state nature of the electrodes of the present invention, an example of a combinature structure having the reference electrode, the ion concentration measuring electrode and the thermal compensator integrated therein is shown in FIG. 3. As in the case of FIGS. 1 and 2, similar reference numbers have been reused in FIG. 3 for common, or similar, elements of the structure but a capital "A" reference letter has been added to some repeated reference numbers to indicate similar elements in adjacent sections of the integrated cell structure shown in FIG. 3. Thus, in the case of a pH electrode, a first substrate 2 of an electrically insulating material has the first chromium layer 4 followed by the silver layer 6 and the silver chloride layer 8 with an outer layer of the selected mismatched temperature coefficient glass 10 to form the reference electrode portion of the integrated cell. A second electrically insulating substrate 2A has a chromium layer 4A followed by a silver layer 6A and a silver chloride layer 8A with a pH glass outer layer 20. A socket shell 24 which may advantageously be a larger size than the socket shell 12 shown in FIGS. 1 and 2 to accommodate an additional number of connector pins is provided adjacent to one side of the aforesaid multilayer structure.

A plurality of electrical connector pins 26, 28, 30 and 32 are located within the connector shell 24. A first one of the pins 26 is connected to the silver layer 6A in the pH measuring electrode section of the integrated multilayer structure by wire 16A. Similarly, the fourth pin 32 is connected by a wire 16 to the silver layer 6 in the reference electrode portion of the integrated multilayer structure. The second and third pins 28 and 30 are connected to a thermal compensator element 34 by separate wires 36 and 38 whereby the thermal compensator element 34 is electrically connected across the second and third pins 28 and 30. The thermal compensator element 34 may be formed in a recess of the second substrate element 2A by any suitable means which can include the same RF sputtering technique used to provide the layers of the pH and reference electrodes structures. Finally, an outer shell, or covering, of a potting compound 40 is provided to enclose the multilayer structure and to secure the pins 26 to 32 while engaging the connector shell 24. A first hole, or window, 19 is provided in the covering 40 to expose the glass layer 10 of the reference electrode while a second opening 19A is provided in the covering 40 to expose the pH glass layer 20 of the pH electrode structure.

MODE OF OPERATION

Since, in the RF sputtering process operation, the operating temperatures are below 200° C., the preparation of the ion responsive electrode structure including the ion responsive glass layer is performed over a much smaller temperature range which further prevents the pH glass from cracking when it is cooled down to room temperature even if the pH glass layer and electrolyte layer do not have an exact temperature coefficient match. Additionally, the thin, i.e., 10,000 Å maximum, glass layer will stretch instead of cracking during temperature cycling to enable the overall multilayer structure to withstand temperature cycling over a relatively wide temperature range, e.g., −70° C. to +200° C. Inherently, the integrated electrode structure has a low impedance due to the thinness of the outer glass layer. Another feature is an extreme ease of replacement whereby the pH electrode, the reference electrode and the thermal compensator can be replaced as a single inexpensive unit. Further, since the delicate glass handling operations required for prior art electrodes have been eliminated, the high manufacturing repeatability of the produce and the reduction of manufacturing rejects enhances the low manufacturing costs of either the separate electrodes shown in FIGS. 1 and 2 or the combinational electrode structure shown in FIG. 3. Finally, in addition to savings in the amount of materials used for the thin layers of the multilayer structure, additional savings will be effected by the elimination of certain expensive metals which were necessary in previous glass electrodes because of the required glass-to-metal seals, e.g., platinum or other similar thermal property metals.

In order to enable the ion responsive electrode of the present invention either in a separate or combination embodiment to measure other than hydrogen ions, the ion responsive layer 20 would be changed to an appropriate ion responsive material. For example to measure fluoride ion concentration, the layer 20 would be lanthanum fluoride. Similarly, for potassium ions, potassium ion selective glass would be used, while for sodium ions, sodium ion selective glass would be used. The method of depositing the various materials for the ion responsive layer would be the same as that disclosed above for the pH electrode and the overall layered electrode structure would also be the same as that disclosed for the pH electrode.

Accordingly, it may be seen that there has been provided, in accordance with the present invention, a solid state ion responsive and reference electrode structure having application in either a separate or a combination electrode construction.

The embodiments of the invention in which an exclusive property or privilege is claimed are defined as follows:

1. A pH electrode comprising
   an electrically insulating substrate,
   a metallic layer on said substrate,
   a solid electrolyte layer on said metallic layer, and
   an RF sputtered pH glass layer on said last-mentioned layer and having a thickness of 10 to 10,000 Angstroms.

2. A pH electrode as set forth in claim 1 wherein said pH glass layer has a coefficient of thermal expansion substantially matched to a coefficient of thermal expansion of said electrolyte layer to maintain the integrity of said pH glass layer.

3. A pH electrode as set forth in claim 1 wherein said metallic layer is silver and said electrolyte layer is silver chloride.

4. A pH electrode as set forth in claim 1 and further including electrical connection means connected to said metallic layer and encapsulating means covering said substrate, said metallic layer and a portion of said pH glass layer while exposing said electrical connection means.

5. A reference electrode comprising
   an electrically insulating substrate,
   a metallic layer on said substrate,
   a solid electrolyte layer on said metallic layer and
   a cracked glass layer on said electrolyte layer and having a coefficient of thermal expansions substantially mismatched with respect to a coefficient of thermal expansion of said electrolyte layer to produce differential expansion therebetween.

6. A reference electrode as set forth in claim 5 wherein said metallic layer is silver and said electrolyte layer is silver chloride.

7. A reference electrode as set forth in claim 5 and further including electrical connection means connected to said metallic layer and encapsulating means encompassing said substrate, said metallic layer, said electrolyte layer and a portion of said glass layer while exposing said electrical connection means.

8. A combination electrode comprising
   an electrically insulating substrate means,
   a first metallic layer on said substrate means,
   a first solid electrolyte layer on said metallic layer,
   a pH glass layer on said electrolyte layer,
   a second metallic layer on said substrate means and electrically insulated from said first metallic layer, said first electrolyte layer and said pH glass layer,
   a second solid electrolyte layer on said second metallic layer and electrically insulated from said first metallic layer, said first electrolyte layer and said pH glass layer, and
   a cracked glass layer on said second electrolyte layer and electrically insulated from said first metallic layer, said first electrolyte layer and said pH glass layer, said second glass layer having a coefficient of thermal expansion mismatched with respect to said second electrolyte layer to produce differential expansion therebetween.

9. A combination electrode as set forth in claim 8 wherein said first and second electrolyte layers are silver chloride and said first and second metallic layers are silver.

10. A combination electrode as set forth in claim 8 wherein said pH glass layer is an RF sputtered glass layer.

11. A combination electrode as set forth in claim 8 and including a thermal compensating means mounted on said insulating substrate and in thermal association therewith while being electrically insulated from said first and second metallic layers, said first and second electrolyte layers and said pH and cracked glass layers.

12. A combination electrode as set forth in claim 8 and further including first electrical connection means connected to said first metallic layer and second electrical connection means connected to said second metallic layer and encapsulating means covering said substrate, said first and second metallic layers, said first and second electrolyte layers and a portion of each of said pH glass layer and said cracked glass layer while exposing said first and second connection means.

13. A combination electrode as set forth in claim 11 and further including first electrical connection means connected to said first metallic layer, second electrical connection means connected to said second metallic layer, third electrical connection means connected to said thermal compensating means and encapsulating means encompassing said substrate, said first and second metallic layers, said first and second electrolyte layers and a portion of each of said pH glass layer and said cracked glass layer while exposing said first, second and third connection means.

14. A combination electrode as set forth in claim 8 wherein said pH glass layer and said second glass layer are each an RF sputtered glass layer.

15. A combination electrode comprising
   an electrically insulating substrate means,
   a first metallic layer on said substrate means,
   a first solid electrolyte layer on said metallic layer,
   a pH glass layer on said electrolyte layer,
   a second metallic layer on said substrate means and electrically insulated from said first metallic layer, said first electrolyte layer and said pH glass layer,
   a second solid electrolyte layer on said second metallic layer and electrically insulated from said first metallic layer, said first electrolyte layer and said pH glass layer, and
   an ion conducting path layer on said second electrolyte layer and electrically insulated from said first metallic layer, said first electrolyte layer and said pH glass layer.

16. A combination electrode as set forth in claim 15 and further including first electrical connection means connected to said first metallic layer, second electrical connection means connected to said second metallic layer and encapsulating means encompassing said substrate, said first and second metallic layers, said first and second electrolyte layers and a portion of each of said pH glass layer and said ion conducting path layer while exposing said first and second conduction means.

17. An ion concentration measuring electrode comprising
   an electrically insulating substrate,
   a metallic layer on said substrate,
   a solid electrolyte layer on said metallic layer, and
   an RF sputtered ion selective layer on said last-mentioned layer.

18. An ion concentration measuring electrode as set forth in claim 17 wherein said ion selective layer has a coefficient of thermal expansion substantially matched to a coefficient of thermal expansion of said electrolyte layer to minimize the differential thermal expansion therebetween to maintain the integrity of said ion selective layer.

19. An ion concentration measuring electrode as set forth in claim 17 and further including electrical connection means connected to said metallic layer, and encapsulating means encompassing said substrate, said metallic layer, said electrolyte layer and a portion of said ion selective layer while exposing said connection means.

20. A combination electrode comprising
an electrically insulating substrate means,
a first metallic layer on said substrate means,
a first solid electrolyte layer on said metallic layer,
an ion selective layer on said electrolyte layer,
a second metallic layer on said substrate means and electrically insulated from said first metallic layer, and first electrolyte layer and said ion selective layer,
a second solid electrolyte layer on said second metallic layer and electrically insulated from said first metallic layer, said first electrolyte layer and said ion selective layer, and
a cracked glass layer on said second electrolyte layer and electrically insulated from said first metallic layer, and first electrolyte layer and said ion selective layer, said cracked glass layer having a coefficient of thermal expansion mismatched with respect to said second electrolyte layer to produce differential expansion therebetween.

21. A combination electrode as set forth in claim 20 wherein said ion selective layer is an RF sputtered layer having a thickness of 10 to 10,000 Angstroms.

22. A combination electrode as set forth in claim 20 and further including first electrical connection means connected to said first metallic layer, second electrical connection means connected to said second metallic layer and an encapsulating means encompassing said substrate, said first and second metallic layers, said first and second electrolyte layers and a portion of each of said ion selective layer and said cracked glass path layer while exposing said first and second connection means.

23. A combination electrode as set forth in claim 20 wherein said ion selective layer and said cracked glass layer are each an RF sputtered layer.

24. A combination electrode comprising
an electrically insulating substrate means,
a first metallic layer on said substrate means,
a first solid electrolyte layer on said metallic layer,
an ion selective layer on said electrolyte layer,
a second metallic layer on said substrate means and electrically insulated from said first metallic layer, said first electrolyte layer and said ion selective layer,
a second solid electrolyte layer on said second metallic layer and electrically insulated from said first metallic layer, said first electrolyte layer and said ion selective layer, and
an ion conducting path layer on said second electrolyte layer and electrically insulated from said first metallic layer, said first electrolyte layer and said ion selective layer.

25. A combination electrode as set forth in claim 24 and further including first electrical connection means connected to said first metallic layer, second electrical connection means connected to said second metallic layer and encapsulating means encompassing said substrate, said first and second metallic layers, said first and second electrolyte layers and a portion of each of said ion selective layer and said ion conducting path layer while exposing said first and second connection means.

26. A combination electrode as set forth in claim 24 wherein said ion selective layer and said ion conducting path layer are each an RF sputtered layer.

27. An ion concentration measuring electrode comprising
a metallic layer,
an electrolyte layer on said metallic layer and
an ion selective layer deposited by RF sputtering on said electrolyte layer and having a thickness of 10 to 10,000 Angstroms.

28. An ion concentration measuring electrode as set forth in claim 27 wherein said metallic layer is silver and said electrolyte layer is silver chloride.

29. An ion concentration measuring electrode as set forth in claim 27 and further including encapsulating means for hermetically sealing and electrically isolating all of said electrolyte layer and a portion of said ion selective layer and said metallic layer while exposing a remaining portion of said ion selective layer and said metallic layer.

30. An ion concentration measuring electrode comprising
an electrolyte layer,
an electrical connection means for providing an electrical connection to said electrolyte layer and
an ion selective layer deposited by RF sputtering on said electrolyte layer spaced from said electrical connection means and having a thickness of 10 to 10,000 Å.

31. An ion concentration measuring electrode as set forth in claim 30 and further including encapsulating means for hermetically sealing and electrically isolating all of said electrolyte layer and a portion of said ion selective layer and said connection means while exposing a remaining portion of said ion selective layer and said connection means.

32. An ion concentration measuring electrode comprising
an electrolyte means for supporting an ion selective layer thereon,
electrical connection means for providing an electrical connection to said electrolyte means and
ion selective layer means deposited by RF sputtering on said electrolyte means spaced from said electrical connection means.

33. An ion concentration measuring electrode comprising
an electrolyte means for supporting an ion selective layer thereon,
electrical connection means for providing an electrical connection to said electrolyte means and
ion selective layer means deposited by RF sputtering on said electrolyte means spaced from said connection means and having a thickness of 10 to 10,000 Å.

34. An ion concentration measuring electrode as set forth in claim 33 and further including encapsulating means for hermetically sealing and electrically isolating all of said electrolyte means and a portion of said ion selective layer means and said connection means while exposing a remaining portion of said ion selective layer means and said connection means.

35. A reference electrode comprising
a metallic layer,
an electrolyte layer on said metallic layer and an ion conducting path layer on said electrolyte layer deposited by RF sputtering.

36. A reference electrode as set forth in claim 35 wherein said ion conducting path layer is a cracked glass layer having a coefficient of thermal expansion substantially mismatched with respect to a coefficient of thermal expansion of said electrolyte layer to produce differential expansion therebetween.

37. A reference electrode as set forth in claim 36 wherein said metallic layer is silver and said electrolyte layer is silver chloride.

38. A reference electrode comprising
an electrolyte layer,
electrical connection means for providing an electrical connection to said electrolyte layer and
an ion conducting path layer on said electrolyte layer deposited by RF sputtering spaced from said connection means.

39. A reference electrode as set forth in claim 38 wherein said ion conducting path layer is a cracked glass layer having a coefficient of thermal expansion substantially mismatched with respect to a coefficient of thermal expansion of said electrolyte layer to produce differential expansion therebetween.

40. A reference electrode comprising
electrolyte means for supporting an ion conducting layer thereon,
electrical connection means for providing an electrical connection to said electrolyte means and
ion conducting path layer means on said electrolyte layer means spaced from said connection means, said ion conducting path layer means being a cracked glass layer having a coefficient of thermal expansion substantially mismatched with respect to a coefficient of thermal expansion of said electrolyte layer to produce differential expansion therebetween.

41. A reference electrode as set forth in claim 40 and further including encapsulating means for hermetically sealing and electrically isolating all of said electrolyte means and a portion of said ion conducting path layer means and said connection means while exposing a remaining portion of said ion conducting path layer means and said connection means.

* * * * *